US010709465B2

(12) United States Patent
Chu et al.

(10) Patent No.: US 10,709,465 B2
(45) Date of Patent: Jul. 14, 2020

(54) RETRIEVAL BASKET AND RELATED METHODS

(71) Applicant: Boston Scientific Scimed, Inc., Maple Grove, MN (US)

(72) Inventors: Michael S. H. Chu, Brookline, MA (US); Peter J. Pereira, Mendon, MA (US); Elizabeth A. Stokley, Baltimore, MD (US); Ronald Ciulla, Westford, MA (US); Colm Long, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 288 days.

(21) Appl. No.: 15/803,307

(22) Filed: Nov. 3, 2017

(65) Prior Publication Data

US 2018/0125511 A1    May 10, 2018

Related U.S. Application Data

(60) Provisional application No. 62/417,574, filed on Nov. 4, 2016.

(51) Int. Cl.
*A61B 17/221* (2006.01)
*A61B 90/00* (2016.01)
(Continued)

(52) U.S. Cl.
CPC ...... *A61B 17/221* (2013.01); *A61B 17/22031* (2013.01); *A61B 90/03* (2016.02);
(Continued)

(58) Field of Classification Search
CPC ................ A61F 2/95; A61F 2002/9517; A61F 2002/011; A61B 17/2902; A61B 17/2841;
(Continued)

(56) References Cited

U.S. PATENT DOCUMENTS 5,830,231 A * 11/1998 Geiges, Jr. ......... A61B 17/2909
606/205
2009/0005754 A1  1/2009 Soetermans
(Continued)

FOREIGN PATENT DOCUMENTS

| WO | 94/18888 A1 | 9/1994 |
| WO | 96/37251 A1 | 11/1996 |
| WO | 2015/134846 A1 | 9/2015 |

OTHER PUBLICATIONS

International Search Report and Written Opinion dated Jun. 8,2018, in International Application No. PCT/US2017/059963 (13 pages).

*Primary Examiner* — Diane D Yabut
*Assistant Examiner* — Majid Jamialahmadi
(74) *Attorney, Agent, or Firm* — Bookoff McAndrews PLLC

(57) ABSTRACT

A medical device may include a sheath, an elongate member at least partially surrounded by the sheath, an end effector at a distal end of the elongate member and movable between an open position and a closed position, and a handle. The handle may include an actuator member coupled to the sheath, an adjustment member, and a biasing member extending between the actuator member and the adjustment member.

13 Claims, 4 Drawing Sheets

(51) Int. Cl.
*A61B 17/22* (2006.01)
*A61B 17/00* (2006.01)

(52) U.S. Cl.
CPC ............... *A61B 2017/00367* (2013.01); *A61B 2017/00477* (2013.01); *A61B 2017/2212* (2013.01); *A61B 2090/032* (2016.02)

(58) Field of Classification Search
CPC ............ A61B 17/22031; A61B 17/221; A61B 17/2912; A61B 17/2913; A61B 17/2916; A61B 17/2845; A61B 17/2212; A61B 17/2215; A61B 17/2217; A61B 17/22034; A61B 17/22035; A61B 90/03; A61B 2090/032
USPC .................................................. 606/113, 127
See application file for complete search history.

(56) References Cited

U.S. PATENT DOCUMENTS

| | | | |
|---|---|---|---|
| 2013/0046297 A1* | 2/2013 | Lingeman | ............ A61B 17/221 606/41 |
| 2014/0257253 A1 | 9/2014 | Jemison | |

\* cited by examiner

RETRIEVAL BASKET AND RELATED METHODS

CROSS-REFERENCE TO RELATED APPLICATIONS

This application claims the benefit of priority to U.S. Provisional Application No. 62/417,574, filed Nov. 4, 2016, which is incorporated by reference herein in its entirety.

TECHNICAL FIELD

Various aspects of the present disclosure relate generally to medical device handles and related methods. More specifically, the present disclosure relates to medical devices and medical device handles for selectively extending and retracting an end effector of an elongate device.

BACKGROUND

Medical devices, such as expandable baskets, retrieval devices, and the like may include an elongate member, and may be arranged for delivery through a working channel of an insertion device (e.g., an endoscope such as, for example, a ureteroscope, a hysteroscope, a bronchoscope, a cystoscope, and similar devices). The elongate member of such medical devices may be selectively extended and retracted relative to the working channel of the insertion device or the device's sheath to deploy or retract the elongate member to perform one or more therapies, treatments, or diagnostic evaluations on a subject. For example, the medical device may include an elongate member that terminates distally at an end effector or an expandable basket and is arranged for delivery through a working channel of a ureteroscope. However, if the end effector or expandable basket is retracted too quickly or compresses too forcefully, the captured material may be broken apart into multiple smaller pieces by the retraction and/or compression. As such, medical professionals may spend time tediously recapturing the smaller pieces of material to remove the material or risk the material remaining in a patient. Such efforts may increase the length, cost, and/or complexity of the medical procedure.

The devices and methods of the current disclosure may rectify some of the deficiencies described above or address other aspects of the prior art.

SUMMARY

Examples of the present disclosure relate to, among other things, medical retrieval devices. Each of the examples disclosed herein may include one or more of the features described in connection with any of the other disclosed examples.

In one example, a medical device may include a sheath, an elongate member at least partially surrounded by the sheath, an end effector at a distal end of the elongate member and movable between an open position and a closed position, and a handle. The handle may include an actuator member coupled to the sheath, an adjustment member, and a biasing member extending between the actuator member and the adjustment member.

The medical device may further include one or more of the following features. The actuator member may include an actuator that is movable within an actuator slot in the handle to move the end effector between the open position and the closed position. The actuator slot may include a closed position, an open position, a lock position, and a release position. The adjustment member may include a protrusion that is received in a slot of the handle. The adjustment member may be slidable to different positions in the slot to selectively adjust the force of the biasing member on the actuator member. The protrusion may be movable within a tab of the slot to lock the adjustment member in a selected position. The adjustment member slot may include a longitudinally extending track and at least two tabs extending normal to the track. The protrusion may be a pin, and the pin may be lockable in the at least two tabs and movable between the at least two tabs through the track. The handle may further include a window through which the adjustment member is accessible. The handle may comprise two radially opposing sides, and the two radially opposing sides of the handle may be mirror images. The end effector may include an expandable retrieval basket. The biasing member may be a compression spring. An equilibrium length of the compression spring may be greater than the distance between the actuator member and the adjustment member. The biasing member may be an elastic band. An equilibrium length of the elastic band may be smaller than the distance between the actuator member and the adjustment member.

In another example, a medical device may include a sheath, an elongate member at least partially surrounded by the sheath, an end effector at a distal end of the elongate member and movable between an open position and a closed position, and a handle. The handle may include an adjustment member slidably disposed in the handle. The adjustment member may include a first spring stop surface, an actuator member coupled to the sheath, the actuator member having a second spring stop surface opposing the first spring stop surface, and a spring biased between the first and second spring stop surfaces.

The medical device may further include one or more of the following features. The actuator member may further include an actuator that is movable within an actuator slot in the handle to move the end effector between the open position and the closed position. The actuator slot may comprise a closed position, an open position, a lock position, and a release position. The adjustment member may include a protrusion that is received in a slot of the handle. The adjustment member may be slidable and lockable in different positions to selectively adjust the force of the spring on the actuator member. The handle may further include a window through which the adjustment member is accessible.

In another example, a method for adjusting a closing force of an end effector of a medical device, where the medical device includes a handle, an actuator member coupled to a sheath, a biasing member, and an adjustment member, may comprise moving the adjustment member longitudinally in the handle to adjust a force provided by the biasing member; and moving an actuator of the actuator member longitudinally in the handle to distally retract the sheath to expose the end effector.

The method for adjusting a closing force of an end effector of a medical device may further include one or more of the following features. Moving the adjustment member longitudinally may include sliding and locking a protrusion of the adjustment member in a slot of the handle. The method may further include capturing a stone or material with the end effector, and allowing the biasing member to provide a restoring force to push the sheath distally toward the end effector.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical device handles for deployment of an elongate member of a medical device. The medical device may be delivered through any appropriate insertion device or alone through a bodily orifice, and may include any type of end effector or retrieval device, such as, e.g., a retrieval basket.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

Figure 1:
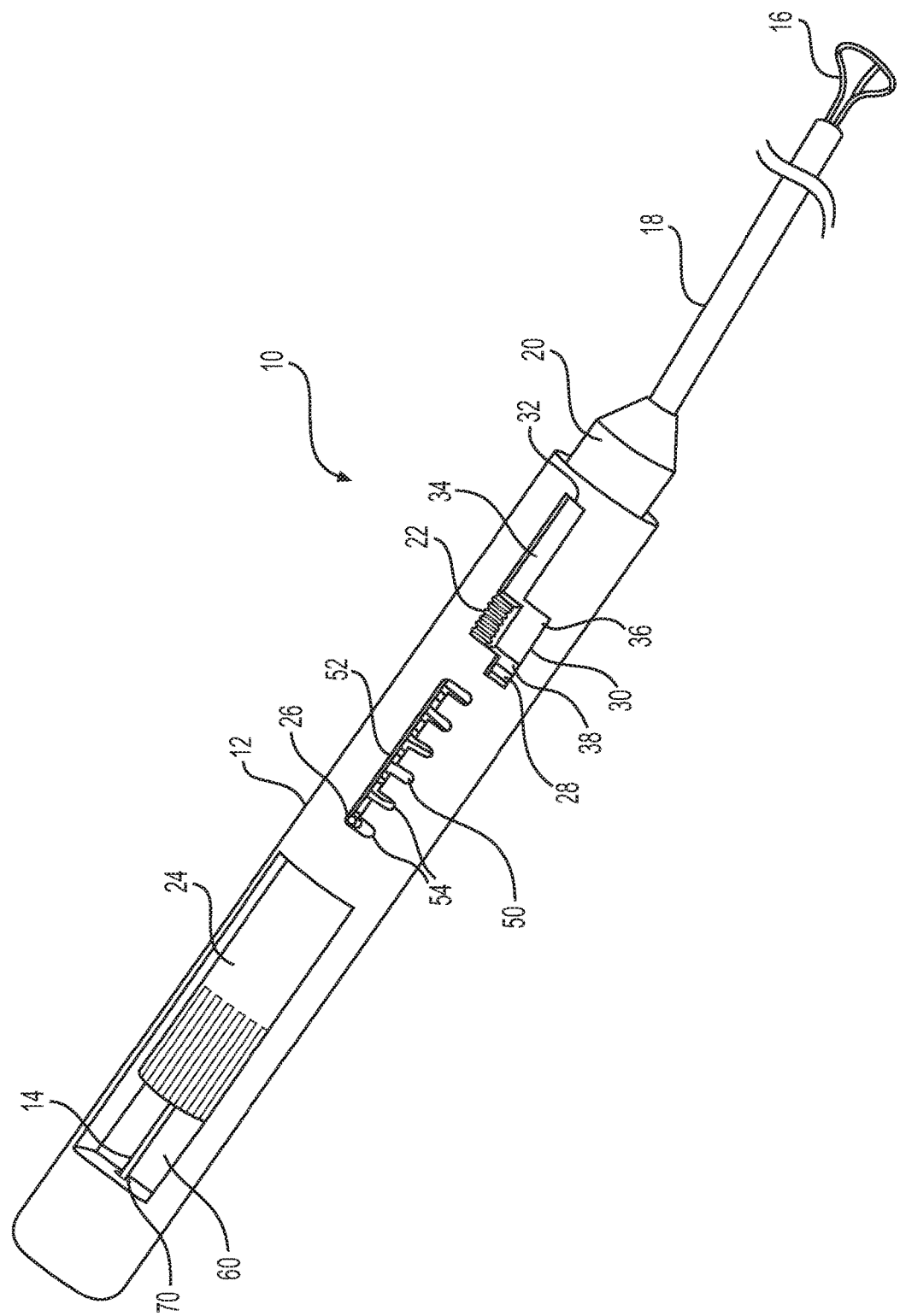
FIG. 1 illustrates an exemplary medical device in an open position.

FIG. 1 illustrates an medical device 10, including a handle 12 and an elongate member 14 terminating distally at an end effector 16. Elongate member 14 may be at least partially surrounded by sheath 18. Sheath 18 may be coupled to an actuator member 20 with an actuator 22. Handle 12 may also enclose an adjustment member 24 with an adjustment member protrusion such as, for example, adjustment member pin 26, along with a biasing member 28 between adjustment member 24 and actuator member 20.

Figure 2:
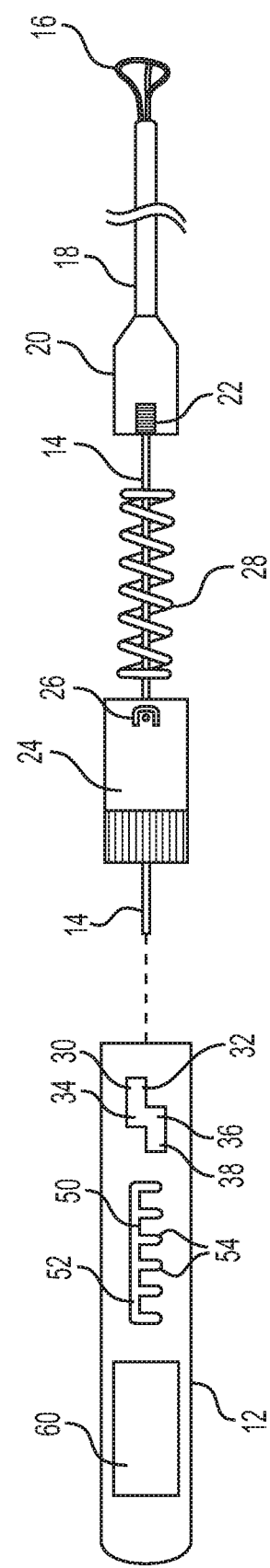
FIG. 2 illustrates an exploded view of the exemplary medical device of FIG. 1.

As shown in FIGS. 1 and 2, handle 12 may include an actuator slot 30, an adjustment member slot 50, and a window 60. Handle 12 may further include a drive wire attachment 70. Proximal end of elongate member 14 may fixedly attach to drive wire attachment 70 after passing through central lumens of the elements enclosed by handle 12. End effector 16 at the distal end of elongate member 14 may be an expandable retrieval basket or other retrieval device. Though not shown, handle 12 may also include a second actuator slot 30', a second adjustment member slot 50', and a second window 60' on an opposite side of handle 12. The additional slots and window on the opposite side of handle 12 allow for more secure locking and accurate adjustments in the slots, easier access and adjustment to adjustment member 24, and prevent cocking of the movable components.

Actuator slot 30 may be in a distal portion of handle 12. Actuator slot 30 may receive actuator 22 of actuator member 20, such that actuator 22 may be selectively manipulated to move within actuator slot 30. Actuator slot 30 may include a closed position 32, an open position 34, a lock position 36, and a release position 38. In one alternate unillustrated embodiment, actuator slot 30 may further include a second lock position 36' and a second release position 38', where second lock position 36' and second release position 38' mirror lock position 36 and release position 38 to allow for both left and right handed locking and releasing.

Figure 3:
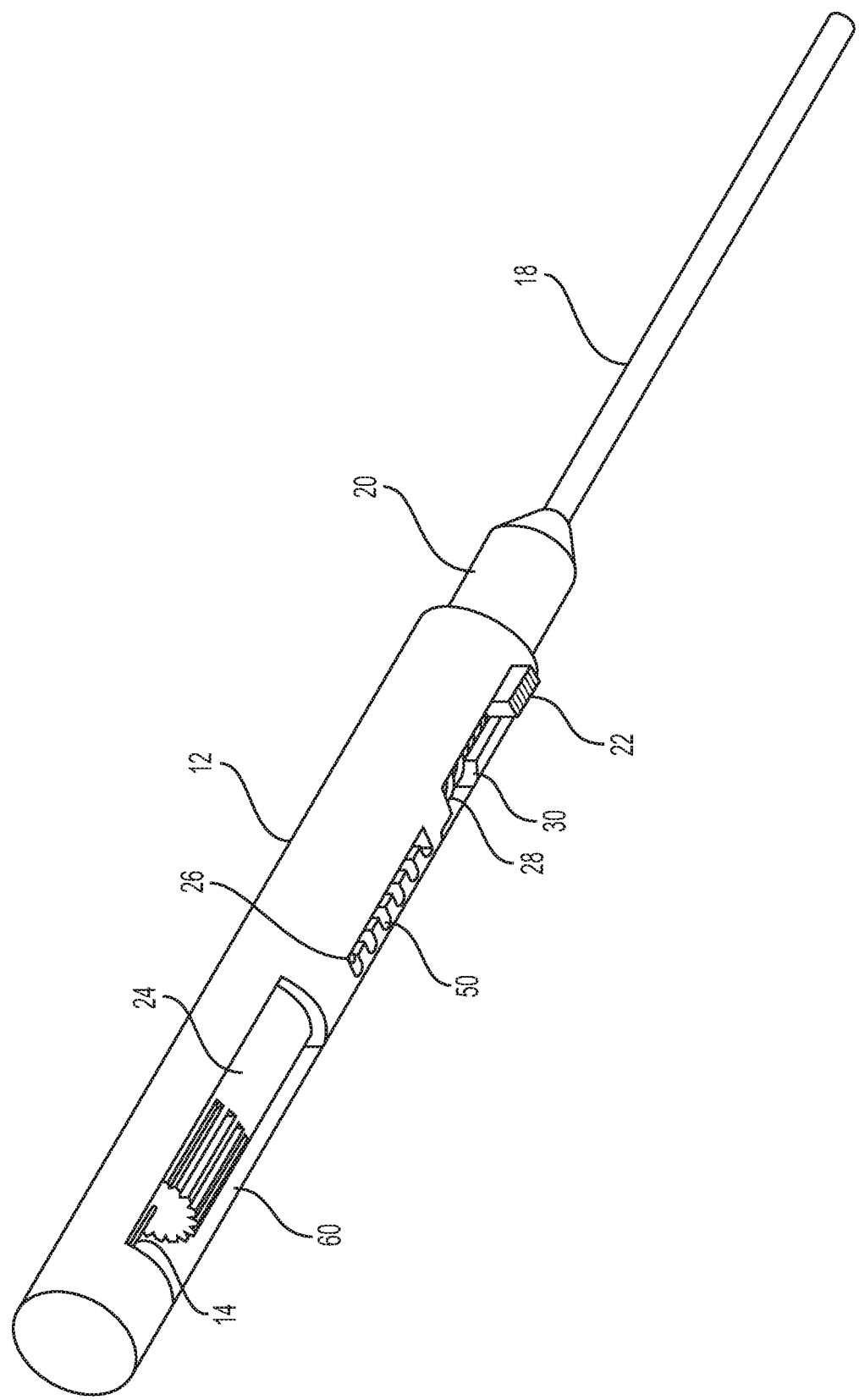
FIG. 3 illustrates a perspective view of medical device of FIG. 1 in a closed position.

Actuator member 20 with actuator 22 may extend distally out of handle 12. The distal portion of actuator member 20 may be coupled to sheath 18, but include a hollow axial lumen such that elongate member 14 may pass through actuator member 20. The proximal face of actuator member 20 may abut the distal portion of biasing member 28. Actuator 22 may be manipulated within actuator slot 30 to manipulate sheath 18 relative to elongate member 14 and end effector 16. For example, actuator 22 may be in closed position 32 such that end effector 16 is enclosed in sheath 18 (FIG. 3). Actuator 22 may be manipulated to open position 34 such that sheath 18 moves proximally to expose end effector 16. Actuator 22 may be manipulated to lock position 36 such that sheath 18 is locked with end effector 16 exposed. Actuator 22 may be manipulated to release position 38 such that sheath 18 moves further proximally, further exposing end effector 16 such that end effector 16 enlarges to release any captured material. Actuator 22 may also include ridges or gripping on the radially outward face to aid in manipulation, as shown in FIG. 3.

Adjustment member slot 50 may be in a middle portion of handle 12, distal to actuator slot 30. Adjustment member slot 50 may receive adjustment member pin 26, and adjustment member pin 26 may be slidably movable within adjustment member slot 50. Adjustment member pin 26 may be formed by a cantilevered protrusion extending radially from adjustment member 24. Adjustment member slot 50 may include an adjustment slot track 52 and a series of tabs 54. Adjustment member pin 26 may be moved into one of tabs 54 to provide a locked position for adjustment member 24. Tabs 54 may be evenly spaced, or may be unevenly spaced. Tabs 54 may be uniformly sized, or tabs 54 may be different sizes to form different locking configurations. Moreover, while six tabs 54 are shown, the invention may include fewer or more tabs 54 to allow variable adjustment of the restoring force provided by biasing member 28. Though not shown, handle 12 may also include a second adjustment member slot 50 with a second adjustment slot track 52' that connects a second series of tabs 54' to receive a second adjustment member pin 26'.

As shown in FIG. 1, adjustment member 24 with adjustment member pin 26 may be positioned in a proximal portion of handle 12. The distal face of adjustment member 24 abuts the proximal portion of biasing member 26. The proximal portion of adjustment member 24 may include a ridged portion accessible through window 60 of handle 12, such that adjustment member pin 26 may be gripped and moved both longitudinally and rotationally by, for example, a user's fingers. Selective positioning of adjustment member pin 26 in one of tabs 54 dictates the restoring force provided by biasing member 28. Adjustment member pin 26 may be selectively locked in one of tabs 54 by action on adjustment member 24 through window 60. Rotation of adjustment member 24 may move adjustment member pin 26 between a tab 54 and track 52 in adjustment member slot 50, such that a distal force may move adjustment member pin 26 towards a more distal tab 54 or a proximal force may move adjustment member pin 26 towards a more proximal tab 54.

As best seen in FIG. 2, biasing member 28 may be a spiral (compression) spring that extends between actuator member 20 and adjustment member 24. Biasing member 28 may have an equilibrium length greater than the distance between the distal face of adjustment member 24, when adjustment member pin 26 is locked in the most proximal tab 54, and the proximal face of actuator member 20 when actuator 22 is in the closed position 32. In operation, adjustment member 24 abuts biasing member 28 and remains longitudinally stationary as adjustment member pin 26 is locked in one of tabs 54. Actuator member 20 compresses biasing member 28 when actuator 22 is moved proximally, such that biasing member 28 provides a restoring force, pushing actuator member 20 distally and actuator 22 towards closed position 32. The restoring force provided by biasing member 28 may be adjusted by selectively positioning adjustment member 24 and locking adjustment member pin 26 in one of tabs 54 in adjustment member slot 50. If adjustment member pin 26 is locked in a more distal tab 54, then biasing member 28 provides a greater restoring force. If, however, adjustment member pin 26 is locked in a more proximal tab 54, then biasing member 28 provides a lesser restoring force because biasing member 28 is closer to its equilibrium length. In one aspect, adjustment member pin 26 may be locked in an even more proximal tab 54 such that biasing member 28 is at equilibrium and provides no restoring force, allowing a user to capture the stone or material with only the force provided by the user's action on actuator 22 for tactile feel.

The adjustable restoring force allows for a user to better tailor a compression force for the sheath 18 and end effector 16 to correspond to the hardness of the stone or material being captured and removed. For example, if the stone or material being captured and removed is hard, a user may position adjustment member pin 26 in a more distal tab 54. If the stone or material being captured and removed is soft and/or fragile, a user may position adjustment member pin 26 in a more proximal tab 54 to ensure that the compression force imparted by the sheath 18 and end effector 16 does not break up the stone or material.

In one aspect, a stone or other material may be removed through the following steps. Medical device 10 may be inserted through an insertion device or through an existing bodily orifice. During insertion, actuator 22 is in closed position 32 such that sheath 18 covers the distal portion of elongate member 14 and end effector 16, as shown in FIG. 3. Medical device 10 may be inserted to a position proximate to the stone or material to be removed. Then, prior to operating actuator 22, a user may adjust the restoring force of biasing member 28, and thus the compression force of end effector 16, by selectively positioning adjustment member pin 26 in one of tabs 54 via adjustment member 24. The restoring force of biasing member 28 may also have been adjustably selected prior to insertion of medical device 10.

With the restoring force selected, a user may operate actuator 22 to move from closed position 32 to open position 34 to pull back sheath 18 and expose end effector 16 to capture the stone or material. A user may also move actuator 22 to lock position 36 to securely position actuator 22, and thus ensure that end effector 16 remains open/exposed, for example, during other maneuvers to capture the stone or material. If the captured stone or material is too large to be retracted or removed with end effector 16, a user may move actuator 22 to release position 38 to further pull back sheath 18, and thus further expose and expand end effector 16, in order to release the large stone or material. If, however, the captured stone or material is not too large, a user may move actuator 22 from lock position 36 back through open position 34 to closed position 32, with biasing member 28 providing the restoring force to push actuator member 20, and thus sheath 18, distally to enclose end effector 16 that now encapsulates the captured stone or material. If the capture was unsuccessful, the above process may be repeated, and the restoring force may also be adjusted via the adjustment member 24 if necessary. The medical device 10 may then be removed from the insertion device or bodily orifice.

Figure 4:
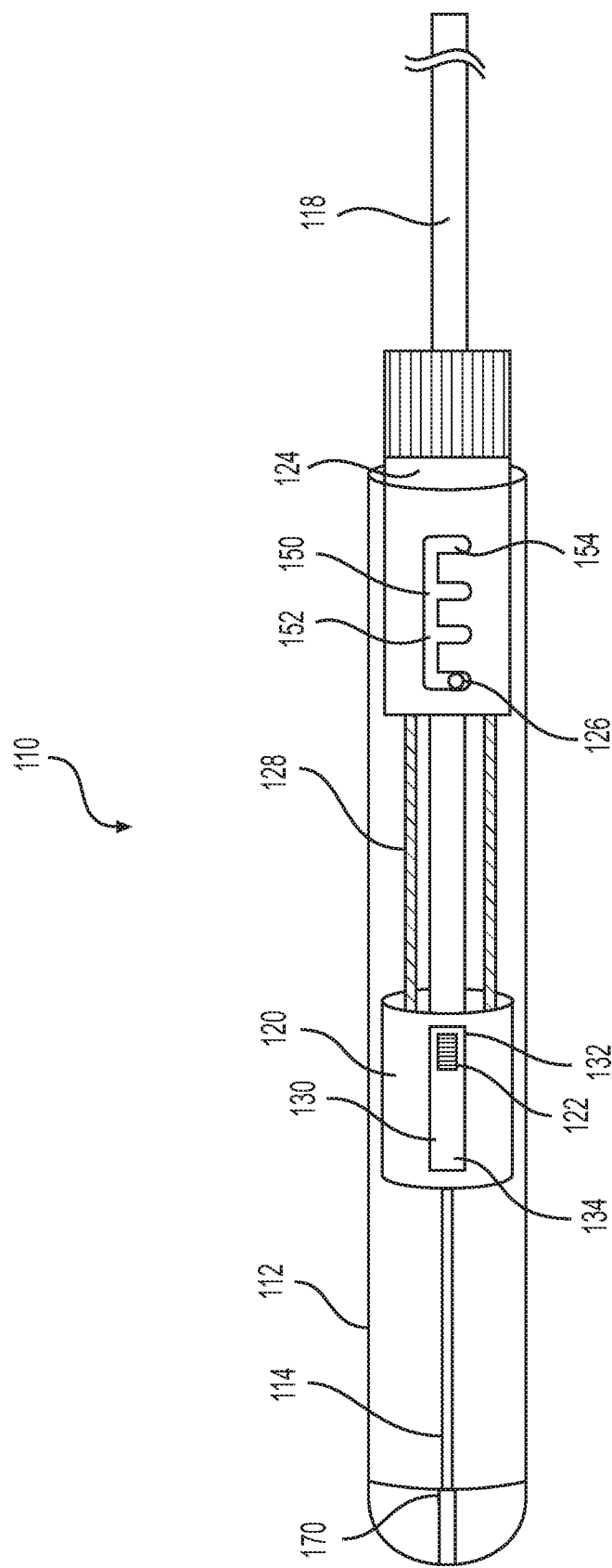
FIG. 4 illustrates an additional exemplary medical device according to aspects of this disclosure.

As shown in FIG. 4, which is an alternative example with similar elements to the medical device 10 shown by 100 added to the reference numbers, a medical device 110 includes an elastic member 128 as a biasing member. Moreover, elastic member 128 serves to pull an actuator member 120 towards an adjustment member 124. Handle 112 in this example includes an adjustment member slot 150 with a track 152 and tabs 154 in a distal portion of the handle, and an actuator slot 130 in a middle portion. Actuator slot 130 may include a closed position 132 and an open position 134, and may include a lock position and a release position (not shown) similar to actuator slot 30. An elongate member 114 is proximally attached to a drive wire attachment 170 in proximal end of handle 112, passes through axial lumens in the elements contained by handle 112, and terminates distally at an end effector 116 (not shown).

Handle 112 may enclose adjustment member 124 with an adjustment member pin 126. A distal portion of adjustment member 124 may extend distally out of handle 112 and include a ridged portion through which a user may manipulate adjustment member 124 and thus selectively move and position adjustment member pin 126 through track 152 and tabs 154 of adjustment member slot 150.

Handle 112 may enclose actuator member 120 with an actuator 122. The distal portion of actuator member 120 is coupled to a sheath 118. Sheath 118 covers elongate member 114 from the distal end of actuator member 120 to and including end effector 116. Sheath 118 also freely passes and travels through an axial lumen in adjustment member 124, so proximal movement of actuator 122 pulls back sheath 118 proximally, exposing and expanding end effector 116. Elastic member 128 then provides a distal restoring force to actuator member 120 to return actuator 122 to closed position 132, thus enclosing end effector 116.

Elastic member 128 may be an elastic band, loop, or strand coupled to adjustment member 124 and to actuator member 120. Elastic member 128 may also be a plurality of elastic bands, loops, or strands. Alternatively, elastic member 128 may be at least one elastic member securely coupled to the interior of adjustment member 124 and actuator member 120. Elastic member 128 may have a molded shape. Elastic member 128 may be rubber, latex, silicone, urethane, or another elastic material. Elastic member 128 may also be a tension spring, and may be metal, such as, for example, stainless steel.

In this example, the stone or material capture and removal process may be carried out as discussed above with selective positioning of adjustment member pin 126 in one of tabs 154 and through action on actuator 122.

In a further alternative example, adjustment members 24 and 124 may include a circumferential threading on at least the distal end or the distal portion. In this example, handles 12 and 112 may include an inner threaded portion that accepts the circumferential threading of the adjustment members 24 and 124. A user may rotate adjustment members 24 and 124 about the mating threads to adjust a force of biasing member 28 or elastic member 128. Adjustment members 24 and 124 and/or handles 12 and 112 may also include markings to correlate a position of the adjustment members 24 and 124 with a corresponding force.

The disclosed medical devices 10 and 110 may help enable quick and reliable capture and removal of a stone or material with end effectors 16 and 116. Tabs 54 and 154 may define incremental, accurately repeatable degrees of restoring forces to ensure that the stone or material to be captured and removed is not crushed or otherwise broken up by the compression and retraction of end effectors 16 and 116. The distance between, number of, and arrangement of tabs 54 and 154 may enable a variety of incremental restoring forces, allowing selection of a desired restoring force of end effectors 16 and 116 in medical devices 10 and 110.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical device, comprising:
   a sheath;
   an elongate member at least partially surrounded by the sheath;
   an end effector at a distal end of the elongate member and movable between an open position and a closed position; and
   a handle, the handle including:
      an actuator member coupled to the sheath;
      an adjustment member; and
      a biasing member between the actuator member and the adjustment member;
   wherein the adjustment member includes a protrusion that is received in a slot of the handle, wherein the protrusion is movable within at least one tab of the slot to lock the adjustment member in a selected position, and wherein the adjustment member is slidable to different positions in the slot to selectively adjust the force of the biasing member on the actuator member.

2. The medical device of claim 1, wherein the actuator member includes an actuator that is movable within an actuator slot in the handle to move the end effector between the open position and the closed position.

3. The medical device of claim 2, wherein the actuator slot comprises a closed position, an open position, a lock position, and a release position.

4. The medical device of claim 1, wherein the slot comprises a longitudinally extending track, and the at least one tab includes at least two tabs extending normal to the track.

5. The medical device of claim 4, wherein the protrusion is a pin, and the pin is lockable in the at least two tabs and movable between the at least two tabs through the track.

6. The medical device of claim 1, wherein the handle further includes a window through which the adjustment member is accessible.

7. The medical device of claim 1, wherein the handle comprises two radially opposing sides, and
   wherein the two radially opposing sides of the handle are mirror images.

8. The medical device of claim 1, wherein the end effector includes an expandable retrieval basket.

9. The medical device of claim 1, wherein the biasing member is a compression spring with an equilibrium length greater than the distance between the actuator member and the adjustment member.

10. A medical device, comprising:
    a sheath;
    an elongate member at least partially surrounded by the sheath;
    an end effector at a distal end of the elongate member and movable between an open position and a closed position; and
    a handle, the handle including:
       an adjustment member, the adjustment member including a first spring stop surface;
       an actuator member coupled to the sheath, the actuator member having a second spring stop surface opposing the first spring stop surface; and
       a spring biased between the first and second spring stop surfaces,
    wherein the adjustment member includes a protrusion that is received in a slot of the handle, wherein the protrusion is movable within at least one tab of the slot to lock the adjustment member in a selected position, and
    wherein the adjustment member is slidable and lockable in different positions in the slot to selectively adjust the force of the spring on the actuator member.

11. The medical device of claim 10, wherein the actuator member further includes an actuator that is movable within an actuator slot in the handle to move the end effector between the open position and the closed position.

12. The medical device of claim 11, wherein the actuator slot comprises a closed position, an open position, a lock position, and a release position.

13. The medical device of claim 10, wherein the handle further includes a window through which the adjustment member is accessible.

* * * * *